United States Patent [19]

Putnam, III

[11] Patent Number: 5,089,231
[45] Date of Patent: Feb. 18, 1992

[54] SAMPLE PLATFORM FOR STABILIZED TEMPERATURE PLATFORM FURNACE

[75] Inventor: Edmund D. Putnam, III, Seward, Ill.

[73] Assignee: Olin Corporation, Cheshire, Conn.

[21] Appl. No.: 488,555

[22] Filed: Mar. 5, 1990

[51] Int. Cl.⁵ .................. G01N 31/12; G01J 3/42
[52] U.S. Cl. .................................. 422/80; 422/69; 422/78; 436/155; 436/179; 356/312
[58] Field of Search ............... 436/155, 179; 422/69, 422/78, 80; 356/312; 266/249, 267; 156/616.3, 617.1; 206/121, 131, 132, 45.19, 45.26, 557

[56] References Cited

U.S. PATENT DOCUMENTS

| | | | |
|---|---|---|---|
| 1,637,260 | 7/1927 | March | 206/131 |
| 2,610,107 | 9/1952 | Dreher | 422/78 |
| 2,811,247 | 10/1957 | Stevenson | 206/121 |
| 3,254,758 | 6/1966 | Guyer | 206/557 |
| 3,767,473 | 10/1973 | Ayel et al. | 156/616.3 |
| 4,303,339 | 12/1981 | Gläser et al. | 356/312 |
| 4,584,275 | 4/1986 | Okano et al. | 435/290 |
| 4,782,953 | 11/1988 | McPhee | 206/557 |
| 4,806,489 | 2/1989 | Beach | 436/155 |
| 4,823,009 | 4/1989 | Biemann et al. | 250/341 |
| 4,826,318 | 5/1989 | Guenther et al. | 356/312 |
| 4,971,438 | 11/1990 | Hütsch et al. | 356/312 |

FOREIGN PATENT DOCUMENTS 97040 6/1984 Japan .................................. 356/312

OTHER PUBLICATIONS

Article entitled "The Stabilized Temperature Platform Furnace" from Atomic Spectroscopy, vol. 2, No. 5, Sep.-Oct. 1981.
Article entitled "Interference in the Analysis of Biological Samples Using the Stabilized Temperature Platform Furnace and Zeeman Background Correction" from Atomic Spectroscopy, vol. 5, No. 3, May-Jun. 1984.
Article entitled "A Survey of Applications of the Stabilized Temperature Platform Furnace and Zeeman Correction" from Atomic Spectroscopy, vol. 6, No. 6, Nov.-Dec. 1985.

Primary Examiner—David L. Lacey
Assistant Examiner—Abanti B. Singla
Attorney, Agent, or Firm—Ralph D'Alessandro

[57] ABSTRACT

An improved sample-holding platform for a stabilized temperature platform furnace in atomic absorption spectroscopy is provided having a recessed base and elevated sidewalls to retain an organic liquid sample and concentrate the atomized elements in a confined area for analysis after vaporization.

6 Claims, 1 Drawing Sheet

SAMPLE PLATFORM FOR STABILIZED TEMPERATURE PLATFORM FURNACE

BACKGROUND OF THE INVENTION

This invention relates generally to stabilized temperature platform furnaces used to analyze organic liquids. More particularly it relates to the design of the L'vov platform used to retain an organic liquid sample in the furnace during direct analysis.

Graphite furnaces with an atmosphere of argon gas are employed with atomic absorption spectroscopy in the semiconductor industry to determine the purity of the chemicals that are used to diffuse onto the silicon oxide in semiconductors during manufacture. The purity of these chemicals is critical, since the presence of impurities will destroy the insulating property of silicon dioxide and cause the semiconductor device to fail.

Current analysis techniques employ the use of indirect chemical analysis or the use of pyrolitic graphite tube furnaces with a centrally located sample platform upon which is Placed the liquid to be analyzed. The indirect analysis technique requires the sample of organic liquid to be evaporated and the residue dissolved into an approximate 0.5 percent nitric acid aqueous solution. This slightly acidic solution is placed on the surface of the sample-holding L'vov platform and then evaporated.

Direct analysis of organic liquids requires multiple deposition and evaporation steps of the organic sample on the L'vov platform. This requires the deposit of relatively small volumetric quantities of the organic sample in droplet form because of the wetability of the L'vov platform used to hold the sample and the sample's tendency to flow off of the platform and reduce the quantity of liquid being analyzed. The organic liquids being analyzed have very low surface tension, compared to water, and the loss of some sample liquid from the platform is possible. To ensure sufficient accuracy of the parts per billion elemental analysis required, up to ten (10) samples of up to ten (10) microliters of the organic liquid have to be manually deposited in droplet form on and evaporated from the L'vov platform. The vapors are analyzed after each cycle. Reproducibility and consistency of the results is a major concern between each run of a multiple deposition-evaporation-analysis cycle. Each deposition in the cycle increases the risk of contamination. Accuracy and sensitivity of the analyses are hampered by the need to perform multiple depositions and evaporations of relatively small samples.

These problems are solved in the design of the present invention which employs an improved L'vov sample-holding platform in a graphite furnace to obtain direct elemental analyses of organic liquids by atomic absorption spectroscopy.

SUMMARY OF THE INVENTION

It is an object of the present invention to provide a sample holding platform in an atomic absorption spectroscopic furnace that permits direct analysis.

It is another object of the present invention to provide a sample holding platform in an atomic absorption spectroscopic furnace that provides subparts per billion determination under stabilized temperature platform furnace (STPF) conditions.

It is a feature of the present invention that the improved sample-holding L'vov platform is employed in a pyrolitic graphite tube atomic absorption spectroscopic furnace.

It is another feature of the present invention that the sample-holding L'vov platform has raised sidewalls and a recessed base to hold the organic liquid sample.

It is another feature of the present invention that the walled platform is open-topped.

It is still another feature of the present invention that the walled platform is machined from a single piece of pyrolitic graphite with the planes of deposition of the pyrolitic graphite parallel to the horizontal plane.

It is an advantage of the present invention that direct organic atomic absorption spectroscopy can be performed with increased sensitivity and greater accuracy.

It is another advantage of the present invention that light primarily impinges on the vaporized sample above the platform within the furnace.

It is another advantage of the present invention that the vaporized elemental atoms are confined in a smaller space during the spectroscopic analysis.

It is still another advantage of the present invention that there is a higher concentration of atomic species immediately above the walled sample-holding platform than is present in prior sample-holding platforms to thereby lower the level of detectability of the atomized species.

It is yet another advantage of the present invention that automatic sampling can be employed.

It is still another advantage in spectroscopic analyses employing the present invention that there is a reduced risk of sample contamination when compared to manual multiple sampling techniques.

These and other objects, features and advantages are obtained in a sample-holding L'vov platform for use in atomic absorption spectroscopic furnaces that has a recessed base and elevated sidewalls to retain the organic liquid sample and concentrate the atomized elements in a confined area for analysis after vaporization.

BRIEF DESCRIPTION OF THE DRAWINGS

The advantages of this invention will become apparent upon consideration of the following detailed disclosure of the invention, especially when it is taken in conjunction with the drawings wherein.

DETAILED DESCRIPTION OF THE PREFERRED EMBODIMENT

Figure 1:
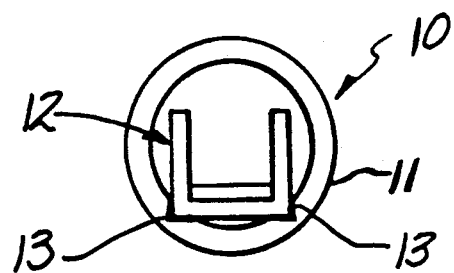
FIG. 1 is a side elevational view of the improved L'vov platform positioned in a pyrolitic graphite tube atomic absorption spectroscopic furnace.

FIG. 1 shows the improved L'vov platform 12 placed within the pyrolitic graphite tube 11 of the graphite tube atomic absorption furnace, indicated generally by the numeral 10.

Figure 2:
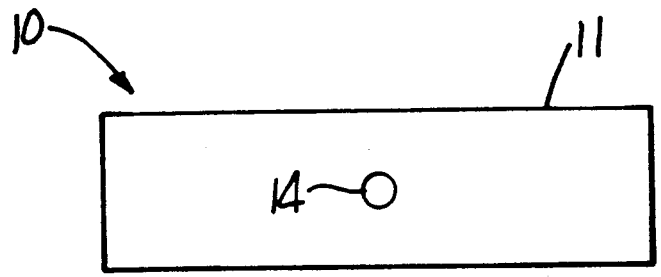
FIG. 2 is a top plan view of the pyrolitic graphite tube atomic absorption spectrographic furnace showing the sample introducing orifice.

FIG. 2 shows top plan view of the furnace 10 with the sample introducing orifice 14 that is present in the top of the pyrolitic graphite tube 11.

Figure 3:
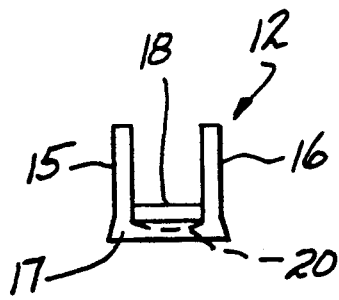
FIG. 3 is side elevational view of the improved sample-holding L'vov platform.

The sample of the organic liquid to be analyzed is inserted by, for example, a Perkin and Elmer Model AS40 Autosampler with adapters, through the orifice 14 so that the sample is placed in the recessed sample-holding trough 20 of FIG. 3 within one millimeter of the sidewalls of the platform 12. The appropriate autosampler, when depositing the organic liquid sample, cannot touch the platform since contact could knock the platform 12 out of the platform retaining grooves 13 that are appropriately formed in the side wall of tube 11 to frictionally maintain the platform 12 in place, nor can it drop the liquid sample from any height because the sample will spatter out of the platform 12 onto the sides of the tube 11.

Figure 4:
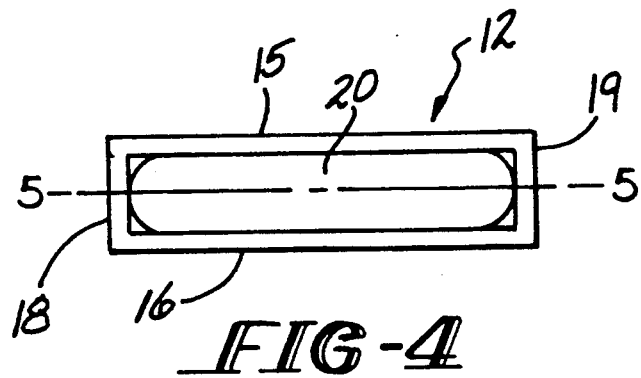
FIG. 4 is top Plan view of the sample-holding L'vov platform.

FIGS. 3 and 4 show the improved L'vov platform 12 in greater detail. First and second opposing elongated high sidewalls 15 and 16 are provided along the longer longitudinal dimension of the platform 12. First and second opposing low end walls 18 and 19 are provided on the opposing ends to thereby complete the surrounding of the recessed sample-holding trough 20 that is machined or otherwise appropriately formed in the platform base 17. First and second opposing low end walls 18 and 19 are substantially lower than the first and second opposing elongated sidewalls 15 and 16, in this case less than half the height, and serve to retain the organic liquid sample on the platform or prevent it from falling off the platform 12 onto the interior walls of tube 11. As designed, the improved platform 12 can hold a volumetric sample of 100 microliters. The platform 12 structure is especially beneficial in obtaining improved and more accurate analysis of the organic liquids because of the height of the first and second opposing elongated high sidewalls 15 and 16 during the evaporation step, as will be explained hereafter.

Figure 5:
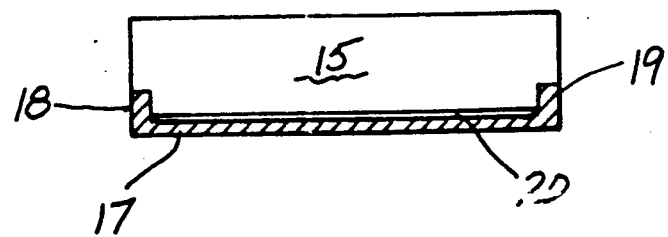
FIG. 5 is a side sectional view taken along the lines 5—5 of FIG. 4.

FIG. 5 shows in sectional side view half of the improved L'vov platform 12 with its improved volume holding capacity. The platform is formed from pyrolitic graphite through the use of vapor deposition of carbon in planes parallel to the horizontal. This repeated horizontal carbon vapor deposition provides a platform that minimizes heating in the furnace by contact of the sample with the tube 11. This also minimizes the carbide formation on the platform and maximizes the vaporization of the atoms found as impurities in the organic liquids being analyzed to increase the efficiency of the operation of the atomic absorption spectroscopic furnace 10 to increase the efficiency of the furnace 10 and thereby increase the sensitivity of the analysis.

In operation, an organic liquid to be analyzed is picked up by an autosampler and is deposited through the sample introducing orifice 14 in the tube 11 onto the recessed sample-holding trouqh 20 in the improved L'vov platform 12. The sample is then taken through distinct and separate steps that includes vaporization of the liquid, pyrolysis of the organic liquids to form atoms and oxides, and vaporization. The temperature within the furnace 10 goes from room temperature to about 2600 degrees Centigrade through the electrical resistance heating of an argon gas atmosphere that is introduced at a flow rate of 300 milliters per minute through the tube 11. Before the temperature gets to approximately 2600 degrees Centigrade and immediately before atomization, the flow of argon gas is automatically shut-off.

The height of the first and second opposing elongated high sidewalls 15 and 16 serves to hold the vaporized atoms in a generally confined area immediately above the platform base 17 of the improved platform 12 to provide a more concentrated atmosphere for the atomic absorption spectroscopy. This also serves to permit light, such as that emanating from the glow of the hot pyrolytic graphite tube 11, to enter only from the top and not from the sides where such background light causes interference with the light to the spectrophotometer. This also reduces the matrix interference caused by background light from the hot graphite tube 11 by allowing light to enter only from the top. Typically, the spectrophotometer can be any suitable commercially available model, such as the Model 6500 Perkin Elmer atomic absorption spectrophotometer, that is used in conjunction with an appropriate graphite stabilized temperature platform furnace, such as the Model HG 500 graphite furnace also available from Perkin Elmer. This equipment can be combined with an appropriate graphics computer for data acquisition.

Use of the improved L'vov platform 12 in the appropriate graphite tube atomic absorption furnace 10 will permit parts per billion levels of analysis of elements including aluminum, iron, zinc, chromium, magnesium, sodium, potassium, lead, gold, copper, and silver. Typical organic liquids analyzed for these impurities include 1,1,1 trichloroethane and tetraethylorthosilicate, which are organic liquid chemicals used as diffusion sources for silicon oxide in the manufacture of semiconductors. Impurities, such as the elements previously recited, when present in sufficient concentrations, will cause a semi-conductor to fail by destroying the insulating properties of the silicon dioxide insulating layer that is placed atop the silicon base layer in a semiconductor. The precise problem occurs when these elements are present in the silicon dioxide base layer since they cause the base layer to leak electrical charge by providing conducting surfaces or pathways through which the conductive integrity of the base and semiconductor is lost. All of the aforementioned elements tend to form a conductive or conducting pathway through the silicon dioxide.

The improved L'vov platform, when used under conditions of stabilized temperature platform furnace operation, will achieve consistent subparts per billion levels of determination of the aforementioned contaminating impurities in the organic chemicals being analyzed. The improved L'vov platform 12 also permits the use of automatic samplers to obtain uniform volume and placement of organic samples in the recessed sample-holding trough 20 without the contamination problems that are associated with manual sample transfers or placements.

While the preferred structure in which the principles of the present invention have been incorporated is shown and described above, it is to be understood the invention is not to be limited to the particular details thus presented, but in fact, widely different means may be employed in the practice of the broader aspects of this invention.

Having thus described the invention, what is claimed is:

1. A graphite tube assembly having a sample-holding platform in combination with an atomic absorption spectroscopic furnace wherein the platform is inserted within the graphite tube atomic absorption spectroscopic furnace, the furnace having a tube with an inlet for insertion of the sample-holding platform and at least one orifice through which a liquid sample is introduced and then vaporized for analysis by atomic absorption spectroscopy, the improvement comprising the sample-holding platform having:

a) an elongated base portion having a top surface constructed so as to receive a low surface tension liquid sample and an opposing bottom surface, parallel first and second longitudinally extending sides, and first and second opposing end sides the parallel first and second opposing end sides intersecting the parallel first and second longitudinally extending sides;

b) the parallel first and second longitudinally extending sides comprising first and second longitudinally extending sidewalls the first and second side walls constructed so as to extend a first distance above the elongated base portion; and c) the first and second opposing end sides further comprising first and second opposing low end walls the first and second end walls constructed so as to extend a second distance above the elongated base portion such that the second distance is less than the first distance, the sidewalls, end walls and top surface of the elongated base portion forming a confined area immediately above the top surface of the elongated base portion within which is contained a concentrated atmosphere of the vaporized liquid sample for atomic absorption spectroscopy.

2. The assembly according to claim 1 wherein the graphite tube has a pair of opposing grooves in its sides within which the platform is slidingly positioned to be maintained in place by friction.

3. The assembly according to claim 2 wherein the graphite is pyrolitic graphite.

4. The assembly according to claim 1 wherein the elongated base portion has a recess therein.

5. The assembly according to claim 4 wherein the recess is trough shaped.

6. The assembly according to claim 5 wherein the parallel first and second longitudinally extending sidewalls are more than twice the distance of the first and second opposing end walls.

* * * * *